US012642637B2

(12) United States Patent
    Simons et al.

(10) Patent No.: US 12,642,637 B2
(45) Date of Patent: Jun. 2, 2026

(54) BIORESORBABLE KNIT FOR HERNIA REPAIR AND METHOD FOR MANUFACTURING THE SAME

(71) Applicant: Sofradim Production, Trévoux (FR)

(72) Inventors: Damien Simons, Lyons (FR); Anthony Mira, Villefranche sur Saone (FR); Julie Lecuivre, Jassans Riottier (FR)

(73) Assignee: SOFRADIM PRODUCTION, Trevoux (FR)

( * ) Notice: Subject to any disclaimer, the term of this patent is extended or adjusted under 35 U.S.C. 154(b) by 781 days.

(21) Appl. No.: 16/582,025

(22) Filed: Sep. 25, 2019

(65) Prior Publication Data
    US 2020/0100883 A1      Apr. 2, 2020

(30) Foreign Application Priority Data
    Sep. 27, 2018    (EP) ..................................... 18306264

(51) Int. Cl.
    *A61F 2/00*        (2006.01)
    *D04B 21/12*       (2006.01)
    *D04B 21/14*       (2006.01)

(52) U.S. Cl.
    CPC .......... *A61F 2/0063* (2013.01); *A61F 2/0077* (2013.01); *D04B 21/12* (2013.01); (Continued)

(58) Field of Classification Search
    CPC .................. A61F 2/0063; A61F 2/0077; A61F 2002/0068; A61F 2220/0016; D04B 21/12; D04B 21/14; D04B 21/04; D04B 1/12; D04B 9/34; D10B 2501/0632; D10B 2509/08; D10B 2403/0144; A61L 27/18; A61L 27/58; A61L 2430/34
See application file for complete search history.

(56) References Cited

U.S. PATENT DOCUMENTS 1,187,158 A      6/1916  Mcginley
1,722,391 A  *   7/1929  Pfrommer .............. D04B 15/80
                                                66/196

(Continued)

FOREIGN PATENT DOCUMENTS

CA      1317836 C      5/1993
CN      103167843 A    6/2013

(Continued)

OTHER PUBLICATIONS

European Search Report for EP 18306264.5 date of completion is Feb. 13, 2019 (3 pages).

(Continued)

*Primary Examiner* — Brian A Dukert
*Assistant Examiner* — Rachel S Highland
(74) *Attorney, Agent, or Firm* — Weber Rosselli & Cannon LLP

(57)                ABSTRACT

The present invention relates to a bioresorbable prosthetic porous knit comprising an arrangement of yarns of bioresorbable biocompatible material defining at least two sides for said knit, said knit being provided, on one of its sides, with barbs protruding outwards from said one side, wherein each yarn of the arrangement defining said two sides is doubled. The invention further relates to a method for manufacturing such a knit.

18 Claims, 3 Drawing Sheets

(52) U.S. Cl.
CPC ...... *D04B 21/14* (2013.01); *D10B 2501/0632*
(2013.01); *D10B 2509/08* (2013.01)

(56) References Cited

U.S. PATENT DOCUMENTS

| | | | |
|---|---|---|---|
| 3,118,294 A | 1/1964 | Van Laethem | |
| 3,124,136 A | 3/1964 | Usher | |
| 3,272,204 A | 9/1966 | Artandi et al. | |
| 3,276,448 A | 10/1966 | Kronenthal | |
| 3,320,649 A | 5/1967 | Naimer | |
| 3,364,200 A | 1/1968 | Ashton et al. | |
| 3,570,482 A | 3/1971 | Shigeru et al. | |
| 4,006,747 A | 2/1977 | Kronenthal et al. | |
| 4,060,081 A | 11/1977 | Yannas et al. | |
| 4,173,131 A | 11/1979 | Melton et al. | |
| 4,193,137 A | 3/1980 | Heck | |
| 4,248,064 A | 2/1981 | Odham | |
| 4,294,241 A | 10/1981 | Miyata | |
| 4,307,717 A | 12/1981 | Hymes et al. | |
| 4,338,800 A | 7/1982 | Matsuda | |
| 4,476,697 A | 10/1984 | Unknown | |
| 4,487,865 A | 12/1984 | Balazs et al. | |
| 4,500,676 A | 2/1985 | Balazs et al. | |
| 4,511,653 A | 4/1985 | Play et al. | |
| 4,527,404 A | 7/1985 | Nakagaki et al. | |
| 4,591,501 A | 5/1986 | Cioca | |
| 4,597,762 A | 7/1986 | Walter et al. | |
| 4,603,695 A | 8/1986 | Ikada et al. | |
| 4,631,932 A | 12/1986 | Sommers | |
| 4,670,014 A | 6/1987 | Huc et al. | |
| 4,709,562 A | 12/1987 | Matsuda | |
| 4,748,078 A | 5/1988 | Doi et al. | |
| 4,759,354 A | 7/1988 | Quarfoot | |
| 4,769,038 A | 9/1988 | Bendavid et al. | |
| 4,796,603 A | 1/1989 | Dahlke et al. | |
| 4,802,346 A * | 2/1989 | Gajjar | D04B 21/18 |
| | | | 66/190 |
| 4,813,942 A | 3/1989 | Alvarez | |
| 4,841,962 A | 6/1989 | Berg et al. | |
| 4,846,815 A | 7/1989 | Scripps | |
| 4,854,316 A | 8/1989 | Davis | |
| 4,925,294 A | 5/1990 | Geshwind et al. | |
| 4,931,546 A | 6/1990 | Tardy et al. | |
| 4,942,875 A | 7/1990 | Hlavacek et al. | |
| 4,948,540 A | 8/1990 | Nigam | |
| 4,950,483 A | 8/1990 | Ksander et al. | |
| 4,970,298 A | 11/1990 | Silver et al. | |
| 5,002,551 A | 3/1991 | Linsky et al. | |
| 5,147,374 A | 9/1992 | Fernandez | |
| 5,162,430 A | 11/1992 | Rhee et al. | |
| 5,171,273 A | 12/1992 | Silver et al. | |
| 5,176,692 A | 1/1993 | Wilk et al. | |
| 5,192,301 A | 3/1993 | Kamiya et al. | |
| 5,196,185 A | 3/1993 | Silver et al. | |
| 5,201,745 A | 4/1993 | Tayot et al. | |
| 5,201,764 A | 4/1993 | Kelman et al. | |
| 5,206,028 A | 4/1993 | Li | |
| 5,217,493 A | 6/1993 | Raad et al. | |
| 5,236,447 A * | 8/1993 | Kubo | A61L 27/14 |
| | | | 623/1.48 |
| 5,254,133 A | 10/1993 | Seid | |
| 5,256,418 A | 10/1993 | Kemp et al. | |
| 5,263,983 A | 11/1993 | Yoshizato et al. | |
| 5,304,595 A | 4/1994 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,334,527 A | 8/1994 | Brysk | |
| 5,339,657 A | 8/1994 | Mcmurray | |
| 5,350,583 A | 9/1994 | Yoshizato et al. | |
| 5,356,432 A | 10/1994 | Rutkow et al. | |
| 5,368,549 A | 11/1994 | Mcvicker | |
| 5,376,375 A | 12/1994 | Rhee et al. | |
| 5,376,376 A | 12/1994 | Li | |
| 5,397,331 A | 3/1995 | Himpens et al. | |
| 5,399,361 A | 3/1995 | Song et al. | |
| 5,413,791 A | 5/1995 | Rhee et al. | |
| 5,425,740 A | 6/1995 | Hutchinson, Jr. | |
| 5,428,022 A | 6/1995 | Palefsky et al. | |
| 5,433,996 A | 7/1995 | Kranzler et al. | |
| 5,441,491 A | 8/1995 | Verschoor et al. | |
| 5,441,508 A | 8/1995 | Gazielly et al. | |
| 5,456,693 A | 10/1995 | Conston et al. | |
| 5,456,711 A | 10/1995 | Hudson | |
| 5,466,462 A | 11/1995 | Rosenthal et al. | |
| 5,480,644 A | 1/1996 | Freed | |
| 5,487,895 A | 1/1996 | Dapper et al. | |
| 5,490,984 A | 2/1996 | Freed | |
| 5,512,291 A | 4/1996 | Li | |
| 5,512,301 A | 4/1996 | Song et al. | |
| 5,514,181 A | 5/1996 | Light et al. | |
| 5,522,840 A | 6/1996 | Krajicek | |
| 5,523,348 A | 6/1996 | Rhee et al. | |
| 5,536,656 A | 7/1996 | Kemp et al. | |
| 5,543,441 A | 8/1996 | Rhee et al. | |
| 5,565,210 A | 10/1996 | Rosenthal et al. | |
| 5,567,806 A | 10/1996 | Abdul-Malak et al. | |
| 5,569,273 A | 10/1996 | Titone et al. | |
| RE35,399 E | 12/1996 | Eisenberg | |
| 5,593,441 A | 1/1997 | Lichtenstein et al. | |
| 5,595,621 A | 1/1997 | Light et al. | |
| 5,601,571 A | 2/1997 | Moss | |
| 5,607,474 A | 3/1997 | Athanasiou et al. | |
| 5,607,590 A | 3/1997 | Shimizu | |
| 5,614,587 A | 3/1997 | Rhee et al. | |
| 5,618,551 A | 4/1997 | Tardy et al. | |
| 5,634,931 A | 6/1997 | Kugel | |
| 5,639,796 A | 6/1997 | Lee | |
| 5,665,391 A | 9/1997 | Lea | |
| 5,667,839 A | 9/1997 | Berg | |
| 5,681,568 A | 10/1997 | Goldin et al. | |
| 5,686,115 A | 11/1997 | Vournakis et al. | |
| 5,690,675 A | 11/1997 | Sawyer et al. | |
| 5,695,525 A | 12/1997 | Mulhauser et al. | |
| 5,697,978 A | 12/1997 | Sgro | |
| 5,700,476 A | 12/1997 | Rosenthal et al. | |
| 5,700,477 A | 12/1997 | Rosenthal et al. | |
| 5,709,934 A | 1/1998 | Bell et al. | |
| 5,716,409 A | 2/1998 | Debbas | |
| 5,720,981 A | 2/1998 | Eisinger | |
| 5,732,572 A | 3/1998 | Litton | |
| 5,749,895 A | 5/1998 | Sawyer et al. | |
| 5,752,974 A | 5/1998 | Rhee et al. | |
| 5,766,246 A | 6/1998 | Mulhauser et al. | |
| 5,766,631 A | 6/1998 | Arnold | |
| 5,769,864 A | 6/1998 | Kugel | |
| 5,771,716 A | 6/1998 | Schlussel | |
| 5,785,983 A | 7/1998 | Furlan et al. | |
| 5,800,541 A | 9/1998 | Rhee et al. | |
| 5,814,328 A | 9/1998 | Gunasekaran | |
| 5,833,705 A | 11/1998 | Ken et al. | |
| 5,840,011 A | 11/1998 | Andgrebe et al. | |
| 5,861,034 A | 1/1999 | Taira et al. | |
| 5,863,984 A | 1/1999 | Doillon et al. | |
| 5,869,080 A | 2/1999 | Mcgregor et al. | |
| 5,871,767 A | 2/1999 | Dionne et al. | |
| 5,876,444 A | 3/1999 | Lai | |
| 5,891,558 A | 4/1999 | Bell et al. | |
| 5,899,909 A | 5/1999 | Claren et al. | |
| 5,906,937 A | 5/1999 | Sugiyama et al. | |
| 5,910,149 A | 6/1999 | Kuzmak | |
| 5,911,731 A | 6/1999 | Pham et al. | |
| 5,916,225 A | 6/1999 | Kugel | |
| 5,919,232 A | 7/1999 | Chaffringeon et al. | |
| 5,919,233 A | 7/1999 | Knopf et al. | |
| 5,922,026 A | 7/1999 | Chin | |
| 5,931,165 A | 8/1999 | Reich et al. | |
| 5,942,278 A | 8/1999 | Hagedorn et al. | |
| 5,962,136 A | 10/1999 | Dewez et al. | |
| 5,972,022 A | 10/1999 | Huxel | |
| RE36,370 E | 11/1999 | Li | |
| 5,993,844 A | 11/1999 | Abraham et al. | |
| 5,994,325 A | 11/1999 | Roufa et al. | |
| 5,997,895 A | 12/1999 | Narotam et al. | |

(56) References Cited

U.S. PATENT DOCUMENTS

| | | | |
|---|---|---|---|
| 6,001,895 A | 12/1999 | Harvey et al. | |
| 6,008,292 A | 12/1999 | Lee et al. | |
| 6,015,844 A | 1/2000 | Harvey et al. | |
| 6,039,686 A | 3/2000 | Robert | |
| 6,042,534 A | 3/2000 | Gellman et al. | |
| 6,042,592 A | 3/2000 | Schmitt | |
| 6,043,089 A | 3/2000 | Sugiyama et al. | |
| 6,051,425 A | 4/2000 | Morota et al. | |
| 6,056,688 A | 5/2000 | Benderev et al. | |
| 6,056,970 A | 5/2000 | Greenawalt et al. | |
| 6,057,148 A | 5/2000 | Sugiyama et al. | |
| 6,063,396 A | 5/2000 | Kelleher | |
| 6,066,776 A | 5/2000 | Goodwin et al. | |
| 6,066,777 A | 5/2000 | Benchetrit | |
| 6,071,292 A | 6/2000 | Makower et al. | |
| 6,077,281 A | 6/2000 | Das | |
| 6,080,194 A | 6/2000 | Pachence et al. | |
| 6,083,522 A | 7/2000 | Chu et al. | |
| 6,120,539 A | 9/2000 | Eldridge et al. | |
| 6,132,765 A | 10/2000 | Dicosmo et al. | |
| 6,143,037 A | 11/2000 | Goldstein et al. | |
| 6,153,292 A | 11/2000 | Bell et al. | |
| 6,158,255 A * | 12/2000 | Ternon | D04B 21/165 |
| | | | 66/193 |
| 6,162,962 A | 12/2000 | Hinsch et al. | |
| 6,165,488 A | 12/2000 | Tardy et al. | |
| 6,171,318 B1 | 1/2001 | Kugel et al. | |
| 6,174,320 B1 | 1/2001 | Kugel et al. | |
| 6,176,863 B1 | 1/2001 | Kugel et al. | |
| 6,179,872 B1 | 1/2001 | Bell et al. | |
| 6,197,325 B1 | 3/2001 | Macphee et al. | |
| 6,197,934 B1 | 3/2001 | Devore et al. | |
| 6,197,935 B1 | 3/2001 | Doillon et al. | |
| 6,210,439 B1 | 4/2001 | Firmin et al. | |
| 6,221,109 B1 | 4/2001 | Geistlich et al. | |
| 6,224,616 B1 | 5/2001 | Kugel | |
| 6,241,768 B1 | 6/2001 | Agarwal et al. | |
| 6,258,124 B1 | 7/2001 | Darois et al. | |
| 6,262,332 B1 | 7/2001 | Ketharanathan | |
| 6,264,702 B1 | 7/2001 | Ory et al. | |
| 6,267,772 B1 | 7/2001 | Mulhauser et al. | |
| 6,277,397 B1 | 8/2001 | Shimizu | |
| 6,280,453 B1 | 8/2001 | Kugel et al. | |
| 6,287,316 B1 | 9/2001 | Agarwal et al. | |
| 6,290,708 B1 | 9/2001 | Kugel et al. | |
| 6,306,424 B1 | 10/2001 | Vyakarnam et al. | |
| 6,312,474 B1 | 11/2001 | Francis et al. | |
| 6,328,686 B1 | 12/2001 | Robert | |
| 6,334,872 B1 | 1/2002 | Termin et al. | |
| 6,383,201 B1 | 5/2002 | Dong | |
| 6,391,333 B1 | 5/2002 | Li et al. | |
| 6,391,939 B2 | 5/2002 | Tayot et al. | |
| 6,408,656 B1 | 6/2002 | Ory et al. | |
| 6,410,044 B1 | 6/2002 | Chudzik et al. | |
| 6,413,742 B1 | 7/2002 | Olsen et al. | |
| 6,428,978 B1 | 8/2002 | Olsen et al. | |
| 6,436,030 B2 | 8/2002 | Rehil | |
| 6,440,167 B2 | 8/2002 | Shimizu | |
| 6,443,964 B1 | 9/2002 | Ory et al. | |
| 6,447,551 B1 | 9/2002 | Goldmann | |
| 6,447,802 B2 | 9/2002 | Sessions et al. | |
| 6,448,378 B2 | 9/2002 | Devore et al. | |
| 6,451,032 B1 | 9/2002 | Ory et al. | |
| 6,451,301 B1 | 9/2002 | Sessions et al. | |
| 6,454,787 B1 | 9/2002 | Maddalo et al. | |
| 6,477,865 B1 | 11/2002 | Matsumoto | |
| 6,479,072 B1 | 11/2002 | Morgan et al. | |
| 6,500,464 B2 | 12/2002 | Ceres et al. | |
| 6,509,031 B1 | 1/2003 | Miller et al. | |
| 6,511,958 B1 | 1/2003 | Atkinson et al. | |
| 6,514,286 B1 | 2/2003 | Leatherbury et al. | |
| 6,514,514 B1 | 2/2003 | Atkinson et al. | |
| 6,540,773 B2 | 4/2003 | Dong | |
| 6,541,023 B1 | 4/2003 | Andre et al. | |
| 6,548,077 B1 | 4/2003 | Gunasekaran | |
| 6,554,855 B1 | 4/2003 | Dong | |
| 6,559,119 B1 | 5/2003 | Burgess et al. | |
| 6,566,345 B2 | 5/2003 | Miller et al. | |
| 6,575,988 B2 | 6/2003 | Rousseau | |
| 6,576,019 B1 | 6/2003 | Atala | |
| 6,596,002 B2 | 7/2003 | Therin et al. | |
| 6,596,304 B1 | 7/2003 | Bayon et al. | |
| 6,599,323 B2 | 7/2003 | Melican et al. | |
| 6,599,524 B2 | 7/2003 | Li et al. | |
| 6,599,690 B1 | 7/2003 | Abraham et al. | |
| 6,613,348 B1 | 9/2003 | Jain | |
| 6,623,963 B1 | 9/2003 | Mueller et al. | |
| 6,630,414 B1 | 10/2003 | Matsumoto | |
| 6,638,284 B1 | 10/2003 | Rousseau et al. | |
| 6,652,594 B2 | 11/2003 | Francis et al. | |
| 6,653,450 B1 | 11/2003 | Berg et al. | |
| 6,656,206 B2 | 12/2003 | Corcoran et al. | |
| 6,660,280 B1 | 12/2003 | Allard et al. | |
| 6,669,735 B1 | 12/2003 | Pelissier | |
| 6,682,760 B2 | 1/2004 | Noff et al. | |
| 6,685,714 B2 | 2/2004 | Rousseau | |
| 6,706,684 B1 | 3/2004 | Bayon et al. | |
| 6,706,690 B2 | 3/2004 | Reich et al. | |
| 6,719,795 B1 | 4/2004 | Bryan et al. | |
| 6,723,335 B1 | 4/2004 | Moehlenbruck et al. | |
| 6,730,299 B1 | 5/2004 | Tayot et al. | |
| 6,736,823 B2 | 5/2004 | Darois et al. | |
| 6,743,435 B2 | 6/2004 | Devore et al. | |
| 6,755,868 B2 | 6/2004 | Rousseau | |
| 6,773,723 B1 | 8/2004 | Spiro et al. | |
| 6,783,554 B2 | 8/2004 | Amara et al. | |
| 6,790,213 B2 | 9/2004 | Cherok et al. | |
| 6,790,454 B1 | 9/2004 | Abdul et al. | |
| 6,800,082 B2 | 10/2004 | Rousseau | |
| 6,833,408 B2 | 12/2004 | Sehl et al. | |
| 6,835,336 B2 | 12/2004 | Watt | |
| 6,852,330 B2 | 2/2005 | Bowman et al. | |
| 6,869,938 B1 | 3/2005 | Schwartz et al. | |
| 6,893,653 B2 | 5/2005 | Abraham et al. | |
| 6,896,904 B2 | 5/2005 | Spiro et al. | |
| 6,936,276 B2 | 8/2005 | Spiro et al. | |
| 6,939,562 B2 | 9/2005 | Spiro et al. | |
| 6,949,625 B2 | 9/2005 | Tayot | |
| 6,966,918 B1 | 11/2005 | Schuldt-Hempe et al. | |
| 6,971,252 B2 | 12/2005 | Therin et al. | |
| 6,974,679 B2 | 12/2005 | Andre et al. | |
| 6,974,862 B2 | 12/2005 | Ringeisen et al. | |
| 6,977,231 B1 | 12/2005 | Matsuda | |
| 6,988,386 B1 | 1/2006 | Okawa et al. | |
| 7,025,063 B2 | 4/2006 | Snitkin et al. | |
| 7,041,868 B2 | 5/2006 | Greene et al. | |
| RE39,172 E | 7/2006 | Bayon et al. | |
| 7,098,315 B2 | 8/2006 | Schaufler | |
| 7,101,381 B2 | 9/2006 | Ford et al. | |
| 7,115,220 B2 | 10/2006 | Dubson et al. | |
| 7,156,858 B2 | 1/2007 | Schuldt-Hempe et al. | |
| 7,175,852 B2 | 2/2007 | Simmoteit et al. | |
| 7,192,604 B2 | 3/2007 | Brown et al. | |
| 7,207,962 B2 | 4/2007 | Anand et al. | |
| 7,214,765 B2 | 5/2007 | Ringeisen et al. | |
| 7,226,611 B2 | 6/2007 | Yura et al. | |
| 7,229,453 B2 | 6/2007 | Anderson et al. | |
| 7,331,199 B2 | 2/2008 | Ory et al. | |
| 7,594,921 B2 | 9/2009 | Browning | |
| 7,615,065 B2 | 11/2009 | Priewe et al. | |
| 7,670,380 B2 | 3/2010 | Cauthen, III et al. | |
| 7,709,017 B2 | 5/2010 | Tayot et al. | |
| 7,713,463 B1 | 5/2010 | Reah et al. | |
| 7,718,556 B2 | 5/2010 | Matsuda et al. | |
| 7,732,354 B2 | 6/2010 | Fricke et al. | |
| 7,785,334 B2 | 8/2010 | Ford et al. | |
| 7,799,767 B2 | 9/2010 | Lamberti et al. | |
| 7,806,905 B2 | 10/2010 | Ford et al. | |
| 7,824,420 B2 | 11/2010 | Eldridge et al. | |
| 7,846,171 B2 | 12/2010 | Kullas et al. | |
| 7,905,825 B2 | 3/2011 | Amal et al. | |
| 7,942,104 B2 | 5/2011 | Butcher et al. | |
| 7,946,236 B2 | 5/2011 | Butcher | |
| 8,074,591 B2 | 12/2011 | Butcher et al. | |

(56) References Cited

U.S. PATENT DOCUMENTS

| | | | |
|---|---|---|---|
| 8,142,515 | B2 | 3/2012 | Therin et al. |
| 8,197,837 | B2 | 6/2012 | Jamiolkowski et al. |
| 8,323,675 | B2 | 12/2012 | Greenawalt |
| 8,366,787 | B2 | 2/2013 | Brown et al. |
| 8,418,508 | B2 | 4/2013 | Lecuivre et al. |
| 8,709,094 | B2 | 4/2014 | Stad et al. |
| 8,834,578 | B2 | 9/2014 | Bayon et al. |
| 8,834,864 | B2 | 9/2014 | Odar et al. |
| 8,846,060 | B2 | 9/2014 | Archibald et al. |
| 8,877,233 | B2 | 11/2014 | Obermiller et al. |
| 8,888,863 | B2 | 11/2014 | Walther et al. |
| 8,956,373 | B2 | 2/2015 | Ford et al. |
| 8,961,850 | B2 | 2/2015 | Wood et al. |
| 9,034,357 | B2 | 5/2015 | Stopek |
| 9,186,235 | B2 | 11/2015 | Ory et al. |
| 9,398,943 | B2 | 7/2016 | Criscuolo et al. |
| 9,445,883 | B2 | 9/2016 | Lecuivre et al. |
| 9,820,843 | B2 | 11/2017 | Greenhalgh et al. |
| 2002/0095218 | A1 | 7/2002 | Carr et al. |
| 2003/0086975 | A1 | 5/2003 | Ringeisen |
| 2003/0114937 | A1 | 6/2003 | Leatherbury et al. |
| 2003/0133967 | A1 | 7/2003 | Ruszczak et al. |
| 2003/0225355 | A1 | 12/2003 | Butler |
| 2004/0034373 | A1 | 2/2004 | Schuldt-Hempe et al. |
| 2004/0054376 | A1 | 3/2004 | Ory et al. |
| 2004/0059356 | A1 | 3/2004 | Gingras |
| 2004/0078089 | A1 | 4/2004 | Ellis et al. |
| 2004/0101546 | A1 | 5/2004 | Gorman et al. |
| 2005/0002893 | A1 | 1/2005 | Goldmann |
| 2005/0021058 | A1 | 1/2005 | Negro |
| 2005/0085924 | A1 | 4/2005 | Darois et al. |
| 2005/0113849 | A1 | 5/2005 | Popadiuk et al. |
| 2005/0137512 | A1 | 6/2005 | Campbell et al. |
| 2005/0142161 | A1 | 6/2005 | Freeman et al. |
| 2005/0148963 | A1 | 7/2005 | Brennan |
| 2005/0175659 | A1 | 8/2005 | Macomber et al. |
| 2005/0228408 | A1* | 10/2005 | Fricke ................... A61F 2/0063 606/151 |
| 2005/0232979 | A1 | 10/2005 | Shoshan |
| 2005/0267521 | A1 | 12/2005 | Forsberg |
| 2005/0288691 | A1 | 12/2005 | Leiboff |
| 2006/0135921 | A1 | 6/2006 | Wiercinski et al. |
| 2006/0147501 | A1 | 7/2006 | Hillas et al. |
| 2006/0216320 | A1 | 9/2006 | Kitazono et al. |
| 2006/0252981 | A1 | 11/2006 | Matsuda et al. |
| 2007/0299538 | A1 | 12/2007 | Roeber |
| 2008/0173223 | A1 | 7/2008 | Butcher et al. |
| 2008/0178786 | A1 | 7/2008 | Butcher |
| 2008/0195231 | A1 | 8/2008 | Ory et al. |
| 2009/0024162 | A1* | 1/2009 | Shalaby ................ A61F 2/0063 606/230 |
| 2009/0138082 | A1 | 5/2009 | Reah et al. |
| 2009/0192532 | A1 | 7/2009 | Spinnler et al. |
| 2009/0193853 | A1 | 8/2009 | Calissoni |
| 2010/0089297 | A1 | 4/2010 | Butcher et al. |
| 2010/0318108 | A1* | 12/2010 | Datta ................... A61L 31/146 156/60 |
| 2012/0179175 | A1* | 7/2012 | Hammell .............. A61F 2/0063 606/151 |
| 2012/0259348 | A1* | 10/2012 | Paul ...................... A61F 2/0063 606/151 |
| 2013/0172915 | A1 | 7/2013 | Thomas et al. |
| 2015/0283305 | A1 | 10/2015 | Li et al. |
| 2015/0315729 | A1 | 11/2015 | Simons |
| 2016/0310262 | A1* | 10/2016 | Doucet ...................... A61F 2/12 |
| 2016/0367351 | A1* | 12/2016 | Lecuivre .............. A61F 2/0063 |
| 2017/0189158 | A1 | 7/2017 | Lecuivre |
| 2018/0110605 | A1 | 4/2018 | Couderc et al. |
| 2018/0271505 | A1 | 9/2018 | Quintero et al. |
| 2018/0303592 | A1* | 10/2018 | Taylor ................... D04B 21/12 |
| 2018/0318059 | A1* | 11/2018 | Couderc .............. A61F 2/0063 |

FOREIGN PATENT DOCUMENTS

| | | | |
|---|---|---|---|
| CN | 104024506 A | 9/2014 |
| CN | 104024508 A | 9/2014 |
| CN | 104302244 A | 1/2015 |
| CN | 105662645 A | 6/2016 |
| CN | 107405425 A | 11/2017 |
| CN | 107708609 A | 2/2018 |
| DE | 19544162 C1 | 4/1997 |
| DE | 10019604 A1 | 10/2001 |
| DE | 10043396 C1 | 6/2002 |
| EP | 0194192 A1 | 9/1986 |
| EP | 0248544 A1 | 12/1987 |
| EP | 0276890 A2 | 8/1988 |
| EP | 0372969 A1 | 6/1990 |
| EP | 0544485 A1 | 6/1993 |
| EP | 0552576 A1 | 7/1993 |
| EP | 0614650 A2 | 9/1994 |
| EP | 0621014 A1 | 10/1994 |
| EP | 0625891 A1 | 11/1994 |
| EP | 0637452 A1 | 2/1995 |
| EP | 0705878 A2 | 4/1996 |
| EP | 0719527 A1 | 7/1996 |
| EP | 0774240 A1 | 5/1997 |
| EP | 0797962 A2 | 10/1997 |
| EP | 0827724 A2 | 3/1998 |
| EP | 0836838 A1 | 4/1998 |
| EP | 0895762 A2 | 2/1999 |
| EP | 0898944 A2 | 3/1999 |
| EP | 1017415 A1 | 7/2000 |
| EP | 1052319 A1 | 11/2000 |
| EP | 1055757 A1 | 11/2000 |
| EP | 1216717 A1 | 6/2002 |
| EP | 1216718 A1 | 6/2002 |
| EP | 0693523 B1 | 11/2002 |
| EP | 1315468 A2 | 6/2003 |
| EP | 1382728 A1 | 1/2004 |
| EP | 1484070 A1 | 12/2004 |
| EP | 1561480 A2 | 8/2005 |
| EP | 1782848 A2 | 5/2007 |
| EP | 2229918 A1 | 9/2010 |
| FR | 2244853 A1 | 4/1975 |
| FR | 2257262 A1 | 8/1975 |
| FR | 2308349 A1 | 11/1976 |
| FR | 2453231 A1 | 10/1980 |
| FR | 2715405 A1 | 7/1995 |
| FR | 2724563 A1 | 3/1996 |
| FR | 2744906 A1 | 8/1997 |
| FR | 2766698 A1 | 2/1999 |
| FR | 2771622 A1 | 6/1999 |
| FR | 2779937 A1 | 12/1999 |
| FR | 2859624 B1 | 12/2005 |
| FR | 2863277 B1 | 6/2006 |
| FR | 2884706 B1 | 4/2008 |
| GB | 2051153 A | 1/1981 |
| JP | H0332677 U | 3/1991 |
| JP | H05237128 A | 9/1993 |
| JP | H09137380 A | 5/1997 |
| JP | 2003530981 A | 10/2003 |
| JP | 2009007682 A | 1/2009 |
| JP | 2014531518 A | 11/2014 |
| JP | 2015151027 A | 8/2015 |
| JP | 2016107086 A | 6/2016 |
| PL | 221 018 B1 | 2/2016 |
| WO | 8902445 A1 | 3/1989 |
| WO | 8908467 A1 | 9/1989 |
| WO | 9012551 A1 | 11/1990 |
| WO | 9206639 A2 | 4/1992 |
| WO | 9220349 A1 | 11/1992 |
| WO | 9311805 A1 | 6/1993 |
| WO | 9318174 A1 | 9/1993 |
| WO | 9417747 A1 | 8/1994 |
| WO | 9507666 A1 | 3/1995 |
| WO | 9518638 A1 | 7/1995 |
| WO | 9532687 A1 | 12/1995 |
| WO | 9603091 A1 | 2/1996 |
| WO | 9608277 A1 | 3/1996 |
| WO | 9609795 A1 | 4/1996 |
| WO | 9614805 A1 | 5/1996 |

(56)                  References Cited

FOREIGN PATENT DOCUMENTS

| | | | |
|---|---|---|---|
| WO | 9641588 | A1 | 12/1996 |
| WO | 9735533 | A1 | 10/1997 |
| WO | 9835632 | A1 | 8/1998 |
| WO | 9849967 | A1 | 11/1998 |
| WO | 9905990 | A1 | 2/1999 |
| WO | 9906079 | A1 | 2/1999 |
| WO | 9906080 | A1 | 2/1999 |
| WO | 9951163 | A1 | 10/1999 |
| WO | 0016821 | A1 | 3/2000 |
| WO | 0067663 | A1 | 11/2000 |
| WO | 0115625 | A1 | 3/2001 |
| WO | 0180773 | A1 | 11/2001 |
| WO | 0181667 | A1 | 11/2001 |
| WO | 0207648 | A1 | 1/2002 |
| WO | 02078568 | A1 | 10/2002 |
| WO | 03002168 | A1 | 1/2003 |
| WO | 2004004600 | A1 | 1/2004 |
| WO | 2004071349 | A2 | 8/2004 |
| WO | 2004078120 | A2 | 9/2004 |
| WO | 2004103212 | A1 | 12/2004 |
| WO | 2005011280 | A1 | 2/2005 |
| WO | 2005013863 | A2 | 2/2005 |
| WO | 2005018698 | A1 | 3/2005 |
| WO | 2005105172 | A1 | 11/2005 |
| WO | 2006018552 | A1 | 2/2006 |
| WO | 2006023444 | A2 | 3/2006 |
| WO | 2009071998 | A2 | 6/2009 |
| WO | 2009031035 | A3 | 1/2010 |
| WO | 2007048099 | A3 | 9/2010 |
| WO | 2011027087 | A1 | 3/2011 |

OTHER PUBLICATIONS

European Search Report with Written Opinion issued in European Patent Application No. EP 21 17 1856 dated Jun. 18, 2021.
Japanese office action issued in Japanese patent application No. 2019-154509 dated Jan. 26, 2024 with English translation.
Notification of the First Office Action issued in Chinese Patent Application No. 201910874667.7 dated Sep. 6, 2023 with English translation.
Japanese Office Action issued in Japanese Patent Application No. 2019-154509 dated Aug. 10, 2023 with English translation.
Examination report No. 1 issued in Australian Patent Application No. 2019222787 dated Apr. 16, 2024.
Notice of Allowance issued in Japanese Patent Application No. 2019-154509 dated Jul. 3, 2024 with English translation.

* cited by examiner

BIORESORBABLE KNIT FOR HERNIA REPAIR AND METHOD FOR MANUFACTURING THE SAME

CROSS-REFERENCE TO RELATED APPLICATION

This application claims benefit of and priority to European Patent Application Serial No. 18306264.5 filed Sep. 27, 2018, the disclosure of the above-identified application is hereby incorporated by reference in its entirety.

TECHNICAL FIELD

The present invention relates to a bioresorbable prosthetic porous knit with outwardly protruding barbs on one side of said knit, showing good mechanical properties and a good elasticity in all directions, and to a method for manufacturing such a knit. The knit obtained by the method of the invention may be used in particular as a wall reinforcement prosthesis, more specifically in ventral hernia repair.

BACKGROUND

The abdominal wall in humans is composed of fat and muscles interconnected by fascias. It sometimes happens that a break in continuity occurs in the fascias, allowing part of the peritoneum to slip through and form a sac, or a hernia, containing either fat or part of the intestines. Hernias show themselves in the form of a bulge at the surface of the skin and are classed, for example, as umbilical or groin hernias or incisional hernias, depending on where they are located. In order to repair a hernia defect, surgeons often fit a textile-based prosthesis in place which replaces or strengthens the weakened anatomical tissues.

Textile-based prostheses are well known in some fields of surgery, such as abdominal wall repair. These prostheses are generally made of biocompatible prosthetic fabric conferring them a certain conformability and they may show a number of shapes, for example rectangular, circular or oval, depending on the anatomical structure to which they are to adapt. Textile-based prostheses are usually made from an arrangement of yarns, such as porous knits which comprise openings and/or pores favoring cellular growth within the knit once the prosthesis is implanted.

Some of these prostheses may be non bioresorbable or semi-bioresorbable, which means that they contain non bioresrobable parts, such as for example non-bioresorbable yarns, which are intended to remain permanently in the body of the patient.

Anyway, in some cases, it may be desirable that the prosthesis does not remain permanently in the body of the patient, for example in a view of avoiding implanting permanent foreign material in the body. In such cases, prostheses which are fully made of bioresorbable yarns are provided. Such bioresorbable prostheses are intended to disappear after they have performed their reinforcing function during the period of cellular colonization, tissue rehabilitation and tissue healing.

Nevertheless, some of the existing bioresorbable prostheses do not maintain sufficient mechanical strength during the months following the implantation. Actually, in order to realize a successful implantation, it is important that the prosthesis promotes gradual transfer of strength from the textile to the functional new tissue. For example, it would be desirable that the textile of the prosthesis carries significant strength during 5 months post implantation and for example residual strength only after 12 months. Ideally, it would be desirable that, after 5 months of implantation, a bioresorbable prosthesis shows a mechanical strength of the order of that usually shown by a non bioresorbable prosthesis at the moment it is implanted.

Indeed, ideally, the prosthesis should provide early support during the critical period of healing. According to some authors (see Williams Z F, Hope W W. *Abdominal wound closure: current perspectives. Open Access Surgery.* 2015:8 p 89-94), healing of abdominal incisions, like any other wounds, requires three phases. The inflammatory phase lasts approximately 4 days, followed by the proliferative phase for 3 weeks. The maturation phase continues for up to a year. By the end of the proliferative phase, the fascia has only 20% of its original strength. At 6 and 20 weeks post-surgery, the fascia has only 50% and 80% of its original strength. In view of this, it can be considered that the critical period of healing lasts at least 5 months.

A prosthesis for hernia repair also needs to be anchored to the abdominal wall. It is known to anchor prostheses to the abdominal wall using surgical suture threads. Anyway, suturing may be time-consuming for the surgeon. It may also create tensions and tearing within the biological tissues. In particular, the abdominal wall is submitted to intraabdominal pressure due to activities, such as coughing, jumping, exercising, breathing, etc. during the daily life of a person. Anchoring a prosthesis by means of suturing may prove to be painful and very unconfortable for the patient in the long term. In view of remedying to this problem, prosthetic knits provided with barbs protruding outwards from one side of the knit have been proposed. These barbs constitute hooks that are able to fix themselves either in another prosthetic fabric, belonging to the same prosthesis or not, or directly in the biological tissues, for example the abdominal wall.

The document WO01/81667 describes the production of a knit comprising barbs on one side of a knit. In this document, the knit is produced using three guide-bars of a knitting machine. Anyway, it has been observed that the knit described in this document may show limited elasticity in some directions.

As seen above, the abdominal wall is submitted to intraabdominal pressure in all directions, said stresses changing directions and intensities at all time in function of the movements and activities of the patient. The prosthesis therefore needs to be able to adapt to these movements and changes of pressure and related stresses by showing a good elasticity in all directions.

SUMMARY

There is a need for a fully bioresorbable porous knit capable of being anchored to the abdominal wall without creating tensions, capable of efficiently reinforcing the abdominal wall at least during 5 months after implantation, while showing sufficient elasticity in all directions, preferably in the warp direction, so that the repaired abdominal wall is capable of smoothly adapting to multidirectional stresses generated by the movements of the patient in his daily life.

The applicant has found a quick and simple method of producing a bioresorbable prosthetic porous knit capable of showing, 5 months after implantation in a body, a mechanical strength of the order of that shown by a non bioresorbable knit at the moment it is implanted, said knit being capable of being anchored to the biological tissue without creating tensions, said knit further showing a good elasticity in all directions.

A first aspect of the invention is a method for manufacturing a bioresorbable prosthetic porous knit comprising an arrangement of yarns of bioresorbable biocompatible material defining at least two sides for said knit, said knit being provided, on one of its sides, with barbs protruding outwards from said one side, said process comprising the following steps:

i) providing a warp knitting machine comprising one needle-bed comprising four guide-bars, namely guide-bar B1, guide-bar B2, guide-bar B3 and guide-bar B4, ii) knitting on said machine yarns of bioresorbable biocompatible material as follows:

Guide-bar B1 is unthreaded,

Guide-bars B2 and B3 are double threaded with yarns of bioresorbable biocompatible material, the knitting patterns followed by guide-bars B2 and B3 involving at least two needles and producing said arrangement of yarns defining said two sides of said knit, Guide-bar B4 is threaded with a hot-melt monofilament yarn of bioresorbable biocompatible material, the knitting pattern followed by guide-bar B4 making stitches generating loops protruding outwards from said one side of said knit, iii) heat-setting the knit obtained at ii), iv) forming barbs by cutting the loops via melting.

By "double threaded bar" is meant according to the present document that two yarns are present in each threaded guide of the bar.

In the present application, a "prosthetic knit" is understood as a knit intended to be implanted in the human or animal body in the form of a prosthesis or any other part designed at least in part with said knit.

Within the meaning of the present invention, «porous knit» means the characteristic whereby a knit has pores, or voids, cells, holes or orifices that are open and distributed uniformly or non-uniformly on the sides of the knit and within its thickness, and that promote cellular colonization. The pores can be present in all sorts of forms, for example spheres, channels and hexagonal shapes.

In the present application, "biocompatible" is understood as meaning that the materials having this property can be implanted in the human or animal body.

The term "bioresorbable" as used herein is defined to include biodegradable, bioabsorbable and bioresorbable materials. By bioresorbable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

Another aspect of the invention is a bioresorbable prosthetic porous knit comprising an arrangement of yarns of bioresorbable biocompatible material defining at least two sides for said knit, said knit being provided, on one of its sides, with barbs protruding outwards from said one side, wherein each yarn of the arrangement defining the two sides of the knit is doubled.

By "the yarn is doubled" is meant in the present document that, during the manufacture of the knit, each threaded guide-bar contributing to the formation of the arrangement defining the two sides of the knit, namely guide-bar B2 and guide-bar B3, receives indeed two yarns instead of one yarn only usually, so that in the end, in the knit obtained, each fibrous path of the arrangement defining the two sides of the knit is formed of two yarns.

Another aspect of the invention is a bioresorbable prosthetic porous knit comprising an arrangement of yarns of bioresorbable biocompatible material defining at least two sides for said knit, said knit being provided, on one of its sides, with barbs protruding outwards from said one side, wherein each yarn of the arrangement defining the two sides of the knit is doubled, said knit further comprising, alternatively or in combination, one or several of the following features:

the yarns of the arrangement defining the two sides of the knit may be monofilaments showing a diameter ranging from about 80 to about 140 μm, preferably showing a diameter of about 125 μm;

the barbs may be formed from monofilaments cuts, wherein the monofilaments show a diameter ranging from about 100 to about 180 rpm, preferably showing a diameter of about 150 μm;

the bioresorbable material may be a copolymer of poly trimethylene carbonate (PTMC) and of poly-L-lactide (PLLA), for example having a composition of 80% lactide and 20% trimethylene carbonate;

the yarns forming the knit and the barbs may be made of a copolymer of poly trimethylene carbonate (PTMC) and of poly-L-lactide (PPLA), for example having a composition of 80% lactide and 20% trimethylene carbonate; and/or the copolymer may show a molar mass Mn ranging from 100,000 to about 225,000;

and/or the copolymer may show a molecular weight Mw ranging from about 100,000 g/mol to about 225,000 g/mol;

the knit may show a gripping strength (N), measured as described in Example 1, ranging from about 60 N to about 160 N, for example from about 70 N to about 150 N, the knit may show a bursting strength (kPa), measured as described in Example 3, ranging from about 400 kPa to about 750 kPa, for example from about 450 kPa to about 700 kPa, the knit may show a tensile breaking strength (N), measured as described in Example 3, ranging from about 200 N to about 500 N, for example from about 240 N to about 380 N, in the warp direction, and ranging from about 200 N to about 400 N, for example from about 250 N to about 360 N, in the weft direction;

the knit may show a tensile elongation under 50 N (%), measured as described in Example 3, ranging from about 20% to about 35%, for example from about 23% to about 32% in the warp direction, and ranging from about 20% to about 45%, for example from about 30% to about 40%, in the weft direction;

the knit may show a tensile breaking elongation (%), measured as described in Example 3, ranging from about 40% to about 100%, for example from about 55% to about 95%, in the warp direction, and ranging from about 60% to about 110%, for example from 70% to 100%, in the weft direction;

the knit may show a tear strength (N), measured as described in Example 3, ranging from about 30 N to about 75 N, for example from about 35 N to about 70 N, in the warp direction, and ranging from about 25 N to about 75 N, for example from about 30 N to about 70 N, in the weft direction;

the knit may show a suture pull out strength (N), measured as described in Example 3, ranging from about 50 N to about 100 N, for example from about 60 N to about 90 N, in the warp direction, and ranging from about 40 N to about 80 N, for example from about 40 N to about 70 N, in the weft direction;

the knit may show a Force max (N) at T0, measured as described in Example 4, ranging from about 300 N to about 600 N, for example from about 350 N to about 550 N;

the knit may show a deflection (mm) at T0, measured as described in Example 4, ranging from about 15 mm to about 30 mm, for example from about 15 mm to about 25 mm;

the knit may show a Force max (N) at T20ws, measured as described in Example 4, ranging from about 300 N to about 600 N, for example from about 350 N to about 550 N;

the knit may show a deflection (mm) at T20ws, measured as described in Example 4, ranging from about 15 mm to about 30 mm, for example from about 15 mm to about 25 mm;

the knit may show a breaking strength (N) at T0, measured as described in Example 5, ranging from about 90 N to about 250 N, for example from about 100 N to about 180 N, in the warp direction, and ranging from about 100 N to about 200 N, for example from about 130 N to about 180 N, in the weft direction;

the knit may show an elongation under 30 N (%) at T0, measured as described in Example 5, ranging from about 15% to about 35%, for example from about 27% to about 35%, in the warp direction, and ranging from about 17% to about 45%, for example from about 25% to about 40%, in the weft direction;

the knit may show an elongation under 50 N (%) at T0, measured as described in Example 5, ranging from about 25% to about 50%, for example from about 35% to about 50%, in the warp direction, and ranging from about 25% to about 55%, for example from about 40% to about 55%, in the weft direction;

the knit may show a breaking elongation (%) at T0, measured as described in Example 5, ranging from about 60% to about 100%, for example from about 65% to about 95%, in the warp direction, and ranging from about 60% to about 110%, for example from about 80% to about 100%, in the weft direction;

the knit may show a breaking strength (N) at T20ws, measured as described in Example 5, ranging from about 90 N to about 250 N, for example from about 100 N to about 180 N, in the warp direction, and ranging from about 100 N to about 200 N, for example from about 130 N to about 180 N, in the weft direction;

the knit may show an elongation under 30 N (%) at T20ws, measured as described in Example 5, ranging from about 15% to about 35%, for example from about 27% to about 35%, in the warp direction, and ranging from about 17% to about 45%, for example from about 25% to about 40%, in the weft direction;

the knit may show an elongation under 50 N (%) at T20ws, measured as described in Example 5, ranging from about 25% to about 50%, for example from about 35% to about 45%, in the warp direction, and ranging from about 25% to about 55%, for example from about 35% to about 55%, in the weft direction;

the knit may show a breaking elongation (%) at T20ws, measured as described in Example 5, ranging from about 60% to about 100%, for example from about 65% to about 97%, in the warp direction, and ranging from about 60% to about 110%, for example from about 80% to about 100%, in the weft direction;

the knit may show a breaking strength (N) at T20wd, measured as described in Example 6, ranging from about 60 N to about 150 N, for example from about 70

N to about 130 N, in the warp direction, and ranging from about 80 N to about 150 N, for example from about 100 N to about 120 N, in the weft direction.

The knit of the invention is produced on a warp knitting machine comprising one needle-bed comprising four guide-bars, namely guide-bar B1, guide-bar B2, guide-bar B3 and guide-bar B4.

The knit of the invention is produced along the warp direction of the machine by means of three guide bars out of four, the guide-bar B1 being unthreaded. Guide-bars B2, B3 and B4 operate together and repeat a knitting pattern defining the evolution of the yarns. The evolution of a yarn from one needle to another is called a course. The needles extend along the width of the machine, which corresponds to the weft direction of the knit produced. The knitting pattern corresponds to the smallest number of courses whereby the whole yarn evolution can be described. The knitting pattern therefore involves a determined number of needles, which corresponds to the total number of needles used for the yarn to complete its whole evolution.

In the method of the invention, the guide-bars B2 and B3, which form the arrangement of yarns defining the two sides of the knit, in other words the ground of the knit from which the barbs issued from guide-bar B4 will protrude, are double threaded. In other words, each threaded guide of these guide-bars is threaded with two yarns. Moreover, the yarns are made of bioresorbable material. This allows the knit obtained by the method of the invention to show, 5 months after implantation, mechanical properties of the order of that shown by a non bioresorbable knit at the moment it is implanted. Moreover, thanks to the presence of the barbs, the knit obtained by the method of the invention is capable of being anchored to the abdominal wall without the use of suturing threads, and therefore without tension. The knit obtained by the method of the invention also shows a good elasticity in all directions, allowing it to conform to the movements of the abdominal wall after implantation, without the patient feeling uncomfortable. Moreover, the barbs of the knit of the invention are also made from bioresorbable material. The knit obtained by the method of the invention is therefore fully bioresorbable and combines the benefits of both synthetic and biologic prostheses.

Guide-bar B4 is preferably single threaded. In embodiments, the knitting pattern of guide-bar B4 includes a succession of stitches and inlays. Such a knitting pattern allows having on one hand some needles producing stitches, and for example, the loops that will give rise to the barbs after melting, and on the other hand some needles not producing stitches and thereby providing enough space for receiving the two yarns coming from the double threaded guide-bars B2 and B3. In particular, the presence of inlays in the knitting pattern of guide-bar B4 facilitates the presence of two yarns in each threaded guide of bars B2 and B3. Indeed, the presence of inlays in the knitting pattern of guide-bar B4 provides needles that are not loaded with stitches and that therefore provide space for fluidly receiving the two yarns coming from bars B2 and B3. The presence of inlays in the knitting pattern of B4, combined to the presence of two yarns in each threaded guide of bars B2 and B3, allows producing a homogeneous knit.

In embodiments, the yarns threaded in guide-bars B2 and B3 are monofilaments showing a diameter ranging from about 80 μm to about 140 μm. For example, these yarns show a diameter of about 125 μm. As a result, the threaded guides of bars B2 and B3 comprise two yarns, each having a diameter of about 125 μm. As seen above, guide-bars B2 and B3 are the guide-bars that form the basis of the knit, from which the barbs issued from the loops generated by guide-bar B4 will protrude. Such embodiments, in which the two yarns threaded in the threaded guides of bars B2 and B3 show a diameter of about 125 μm, allow producing a knit that shows good mechanical strength. In particular, thanks to the presence of inlays in the knitting pattern of bar B4, the two yarns of diameter 125 μm of each threaded guide of bars B2 and B3 can be fluidly received in the needles concerned by said inlays.

In embodiments, the yarns threaded in guide-bar B4 are monofilaments showing a diameter ranging from about 100 μm to about 180 μm. For example, these yarns show a diameter of about 150 μm. Such monofilaments allow providing barbs showing a good gripping force.

In embodiments, the knitting pattern repetition unit for guide-bars B2 and B3 includes a displacement of the yarns on 5 to 9 needles along a first number of courses and a displacement of the yarns on 2 needles only along a second number of courses. For example, the first number of courses is between 4 and 6, and the second number of courses is between 2 and 4. For example, the knitting pattern repetition unit for guide-bars B2 and B3 includes a displacement of the yarns on 7 needles along 4 courses and a displacement of the yarns on 2 needles only along 2 courses. Such embodiments allow producing a knit having particularly good elongation properties, and therefore good elasticity in all directions, while showing good mechanical properties, in particular excellent tensile breaking strength and bursting strength, good tear strength and suture pull-out strength.

In embodiments, guide-bars B2 and B3 are double threaded one full, two empty, according to the following pattern according to the standard ISO 11676 (publication year 2014):

B2: 0-1/3-4/7-6/4-3/0-1/2-1//

B3: 7-6/4-3/0-1/3-4/7-6/5-6//

This knitting pattern repetition unit of guide-bars B2 and B3 includes a displacement of the yarns on 7 needles along 4 courses and a displacement of the yarns on 2 needles only along 2 courses.

In such embodiments, guide-bar B4 may be threaded one full, two empty according to the following pattern according to the standard ISO 11676 (publication year 2014):

B4: 4-4/1-2/0-1/2-1/4-4/2-2//

Such a knitting pattern produces a succession of stitches and inlays.

With the knitting patterns as described above for B2, B3 and B4, it is possible to obtain a knit having good mechanical properties together with a good elasticity in all directions.

In other embodiments, the knitting pattern repetition unit for guide-bars B2 and B3 includes a displacement of the yarns on 4 needles. Such embodiments allow producing a knit having particularly good elasticity in all directions, while showing good mechanical properties.

For example, guide-bars B2 and B3 may be double threaded one full, two empty, according to the following pattern according to the standard ISO 11676 (publication year 2014):

B2: 1-0/3-4//

B3: 3-4/1-0//

In such embodiments, guide-bar B4 may be threaded one full, two empty according to the following pattern according to the standard ISO 11676 (publication year 2014):

B4: 5-5/2-3/0-0/3-2//

Such a knitting pattern produces a succession of stitches and inlays.

With the knitting patterns as described above for B2, B3 and B4, it is possible to obtain a knit having good mechanical properties together with a good elasticity.

Bioresorbable materials suitable for the yarns and the barbs of the knit of the present invention include polylactic acid (PLA), polyglycolic acid (PGA), oxidized cellulose, polycaprolactone (PCL), polydioxanone (PDO), trimethylene carbonate (TMC), polyvinyl alcohol (PVA), polyhydroxyalkanoates (PHAs), copolymers of these compounds and mixtures thereof.

A preferred bioresorbable biocompatible material suitable for the yarns and the barbs of the knit of the present invention is a polyhydroxyalkanoate such as a copolymer of poly trimethylene carbonate (PTMC) and of poly-L-lactide (PLLA). The copolymer may have a composition of about 80% lactide and 20% trimethylene carbonate. For example, the polymer structure is a triblock copolymer with a central bloc of poly trimethylene carbonate (PTMC) and two lateral blocks of poly-L-lactide (PLLA) as shown below under Formula (I):

$$H{-}\left[O{-}\underset{CH_3}{\overset{}{CH}}{-}\underset{O}{\overset{}{C}}{-}O{-}\underset{CH_3}{\overset{}{CH}}{-}\underset{\underset{O}{\|}}{C}{-}\right]_m\left[O{-}CH_2CH_2CH_2{-}O{-}\underset{\underset{O}{\|}}{C}\right]_n\left[O{-}\underset{CH_3}{\overset{}{CH}}{-}\underset{\underset{O}{\|}}{C}{-}O{-}\underset{CH_3}{\overset{}{CH}}{-}\underset{\underset{O}{\|}}{C}\right]_m H \qquad (I)$$

The polymer of formula (I) above may show a molar mass $M_n$ ranging from about 100,000 to about 225,000 and a molecular weight $M_w$ ranging from about 100,000 g/mol to about 225,000 g/mol.

In a preferred embodiment, the bioresorbable biocompatible material forming the yarns and the barbs of the knit of the invention is a triblock copolymer with a central bloc of poly trimethylene carbonate (PTMC) and two lateral blocks of poly-L-lactide (PLLA) having a composition of about 80% lactide and 20% trimethylene carbonate.

The polymer may be manufactured in a dry stainless steel conical vessel reactor outfitted with two helicone-style mixing blades, under dry conditions (nitrogen gaz) by first adding trimethylene carbonate, di-functional initiator (diethylene glycol) and catalyst (Stannous octoate), which are polymerized by heating. After complete polymerization (first stage) the lactide may be added (with additional catalyst). When the reaction is complete the polymer may be extruded, pelletized and dried (to remove moisture and monomer) under heat and vacuum.

For example, the co-polymer may then be melt above the fusion temperature to be extruded through the spinneret, to produce yarns. The yarns produced may show a diameter ranging from 80 μm to 200 μm. For example, yarns of diameter 125 μm and of diameter 150 μm may be produced. The yarns are cooled in water just after their extrusion.

Monofilaments are then going through a succession of oven and rolls systems to stretch them and reach their technical characteristics. Both 125 μm diameter yarns and 150 μm diameter yarns may be warped onto beams that will further be set onto the warp knitting machine.

Further to the knitting step as described above, the knit obtained is heat-set. The heat-setting step allows stabilizing the knit in width and length, in particular in the weft direction and in the warp direction. The heat-setting step may be performed at a temperature ranging from about 100° C. to about 125° C., for example at about 115° C. In embodiments, the temperature at which the heat-setting step is performed is below the melting point of the hot-melt material forming the monofilament threaded in guide-bar B4, preferably at least about 10° C. below said melting point. The knit may be kept under no tension, neither in the warp direction nor in the weft direction, during the heat-setting step.

In a further step, the loops generated by the hot-melt monofilament threaded in guide-bar B4 are cut to form the barbs. The loops are cut via melting the monofilament.

In embodiments, this step is performed by placing the side of the knit provided with the protruding loops on a cylinder that is brought to a temperature that causes the loops to melt so they are cut in two and thus form the barbs, as described in WO01/81667. This cutting generates two barbs, each of them having a head with dimensions usually greater than its stem.

The barbs obtained are particularly efficient for gripping biological tissues, such as muscles, connective tissues, etc. . . .

The knit may then be cleaned and sterilized according to conventional sterilization methods, for example using ethylene oxide.

The knit of the invention may be used on its own or as a part of a prosthesis for wall reinforcement in parietal or visceral surgery, in particular for the treatment of hernias, preferably ventral hernias.

Another aspect of the invention is a prosthesis for the treatment of hernias, comprising at least one knit as described above. The prosthesis of the invention shows good mechanical properties, such as tensile strength, as well as good elongation properties, such as tensile elongation strength. In particular, the prosthesis of the invention shows particularly good ball burst properties, allowing it to show a high mechanical resistance together with adequate elasticity. The prosthesis of the invention therefore ensures efficient reinforcement of the abdominal wall, with an optimal comfort for the patient, as the elasticity of the prosthesis allows it to adapt and smoothly respond to the intraabdominal pressure generated by the movements of the patient in his daily life.

BRIEF DESCRIPTION OF THE DRAWINGS

The knit of the invention and the method for manufacturing said knit will be further described in details with reference to the examples below and enclosed drawings in which.

DETAILED DESCRIPTION OF EMBODIMENTS

Example 1

A prosthetic knit according to the invention, hereinbelow referred to as Knit A, is produced on a warp knitting machine with four guide bars B1, B2, B3 and B4, as described above, where the bar B1 is in position 1 on the knitting machine, the bar B2 is in position 2, the bar B3 is in position 3, and the bar B4 is in position 4.

Guide-bar B1 is unthreaded.

Guide-bars B2 and B3 are double threaded one full, two empty, according to the following knitting pattern according to the standard ISO 11676 (publication year 2014):

B2: 0-1/3-4/7-6/4-3/0-1/2-1//
B3: 7-6/4-3/0-1/3-4/7-6/5-6//

Figure 1:
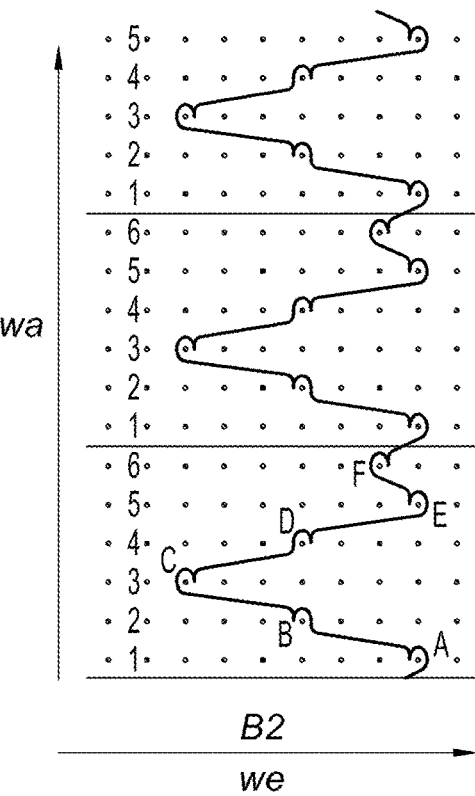
FIG. 1 is a schematic representation of the knitting pattern of Guide-bar B2 according to a first embodiment of the knit of the invention.

The knitting pattern of guide-bar B2 is shown on FIG. 1 according to a representation well known from persons skilled in the art, where "wa" indicates the warp direction and "we" indicates the weft direction.

Figure 2:
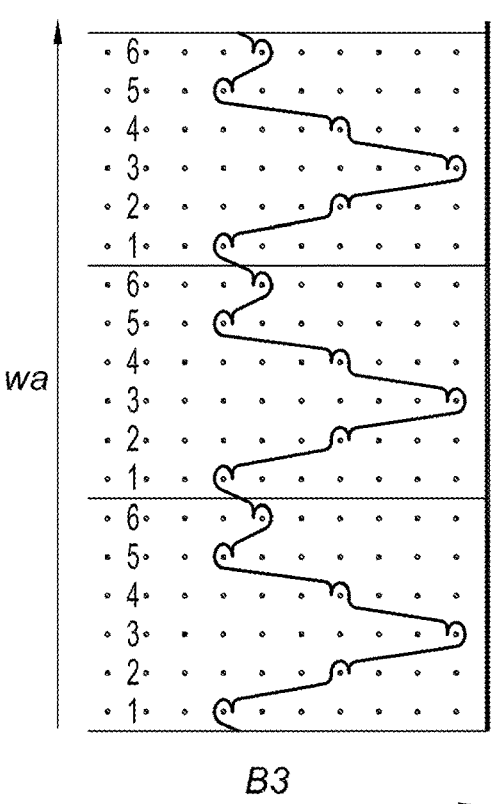
FIG. 2 is a schematic representation of the knitting pattern of Guide-bar B3 according to the first embodiment of the knit of the invention.

The knitting pattern of guide-bar B3 is shown on FIG. 2 according to a representation well known from persons skilled in the art, where "wa" indicates the warp direction and "we" indicates the weft direction.

Guide-bar B4 is threaded one full, two empty, according to the following knitting pattern according to the standard ISO 11676 (publication year 2014):

B4: 4-4/1-2/0-1/2-1/4-4/2-2//

Figure 3:
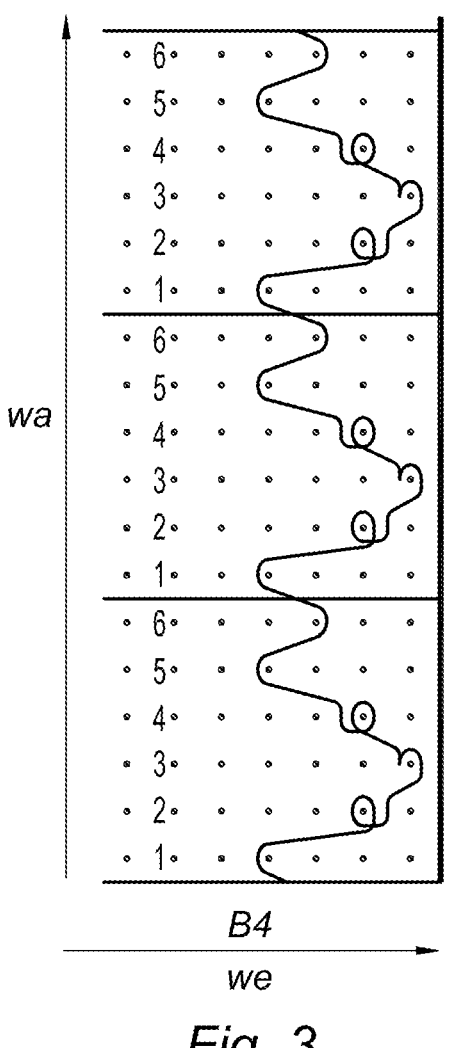
FIG. 3 is a schematic representation of the knitting pattern of Guide-bar B4 according to the first embodiment of the knit of the invention.

The knitting pattern of guide-bar B4 is shown on FIG. 3 according to a representation well known from persons skilled in the art, where "wa" indicates the warp direction and "we" indicates the weft direction.

All the yarns used in manufacturing the present Knit A, namely the yarns threaded in guide-bars B2, B3 and B4, are made of a triblock copolymer with a central bloc of poly trimethylene carbonate (PTMC) and two lateral blocks of poly-L-lactide (PLLA) having a composition of about 80% lactide and 20% trimethylene carbonate. Knit A is fully bioresorbable.

The yarns threaded in guide-bars B2 and B3 are monofilaments having a diameter of 125 μm. The yarn count is 156 dtex. Each threaded guide is threaded with two yarns.

The yarns threaded in guide-bar B4 are monofilaments having a diameter of 150 m. The yarn count is 227 dtex. Guide-bar B4 is single threaded.

For each FIG. 1-3, the graphic shows the movement of the corresponding guide-bar. The guide-bar's movement is read from bottom to top, the first knitted course being at the bottom.

The global pattern repetition size of each guide-bar is 6 courses, so that the overall pattern repetition size is 6 courses (lines named 1' to 6' in FIG. 1).

The yarns threaded in B2 and B3 constitute the base of the present knit, since the hot-melt monofilament yarn, intended to generate the barbs, will be regularly cut during the melting step. The knitting patterns of guide-bars B2 and B3 produce an arrangement of yarns defining the two sides of the knit.

The knitting pattern repetition unit for guide-bars B2 and B3 includes a displacement of the yarns on 7 needles along 4 courses (corresponding to the displacement referred to as A-B-C-D on FIG. 1) and a displacement of the yarns on 2 needles only along 2 courses (corresponding to the displacement referred to as E-F on FIG. 1).

Sequence A-B-C-D brings some strength to the knit in the weft direction, while the sequence E-F brings some performance to the knit in the warp direction.

Such a knitting pattern repetition unit allows producing a knit having particularly good elasticity in all directions, while showing good mechanical properties, in particular excellent tensile breaking strength and bursting strength, good tear strength and suture pull-out strength.

The knitting pattern followed by guide-bar B4 makes stitches generating loops protruding outwards from one side of the knit.

Once the knit is produced, it is heat-set according to a conventional method, for example at 115° C., in order to stabilize it in length and width.

After the heat-setting step, the side of the knit from which the loops produced by guide-bar B4 protrude is placed in contact with a cylinder containing a heating resistor so as to melt the loops, for example in the same manner as described in WO01/81667. The melting point of the copolymer of 80% lactide and 20% trimethylene carbonate used in the present example for forming the barbs being 172° C., the heating resistor may show a temperature of about 250-290° C.

On melting, each loop cuts in two and gives rise to two barbs protruding outwards from said side of the knit.

The following properties of Knit A of the present example have been determined as follows:

Surface density (g/m$^2$): measured according to ISO 3801: 1977«Determination of mass per unit length and mass per unit area», 5 samples, 1 dm$^2$ disk, pore size (width×height) (mm): knit biggest pores width and height are measured making one measurement on 5 individual samples of dimensions 100×50 mm, with a profile projector such as a projector, Gripping strength (N): the knit samples to be tested are evaluated in combination with counter-samples made of textile having hexagonal shaped pores. The knit samples are first anchored to the counter-samples thanks to their barbs as follows: counter-samples of dimensions 5×10 cm are prepared; knit samples of dimensions 5×10 cm are prepared; each counter-sample is laid on a horizontal plane, with the hexagonal shaped pores upwards; a knit sample is positioned on top of the counter-sample, with the barbs protruding downwards; the knit sample is then pressed onto the counter-sample by passing a load of 1.5 kg back and forth 5 times on the knit sample; the counter-sample and the knit sample gripped thereto are then positioned between a sliding plate and a tightening plate of dimensions 5×5 cm; the assembly is then mounted on a traction testing machine such as the Hounsfield model H5KS (Hounsfield, Redhill, England) provided with a fixed jaw and a mobile jaw; the counter-sample is attached to the mobile jaw and the knit sample is attached to the fixed jaw: the preload is set at 2 N; the mobile jaw is moved away from the fixed jaw at a speed of 100 mm/min; the gripping strength is the maximum shear force measured before the knit sample fails and/or slides on the counter-sample. The collected value represents the average of 5 samples.

The results are collected in Table I below:

TABLE I

| Property | Knit A |
| --- | --- |
| Surface density (g/m$^2$) | 200 |
| Pore size (mm$^2$) (width × height) | 1.3 × 2.3 |
| Gripping strength (N) | 112 ± 5 |

Example 2

A prosthetic knit according to the invention, referred to herein below as Knit B, is produced on a warp knitting machine with four guide bars B1, B2, B3 and B4, as described above, where the bar B1 is in position 1 on the knitting machine, the bar B2 is in position 2, the bar B3 is in position 3, and the bar B4 is in position 4.

Guide-bar B1 is unthreaded.

Guide-bars B2 and B3 are double threaded one full, two empty, according to the following knitting pattern according to the standard ISO 11676 (publication year 2014):

B2: 1-0/3-4//

B3: 3-4/1-0//

Guide-bar B4 is threaded one full, two empty, according to the following knitting pattern according to the standard ISO 11676 (publication year 2014):

B4: 5-5/2-3/0-0/3-2//

Figure 4:
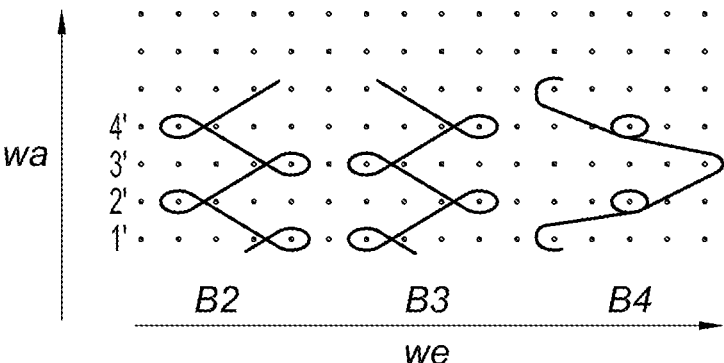
FIG. 4 is a schematic representation of the knitting patterns of guide-bars B2, B3 and B4 of a second embodiment of the knit of the invention.

The knitting patterns of guide-bars B2, B3 and B4 are shown on FIG. 4 according to a representation well known from persons skilled in the art, where "wa" indicates the warp direction and "we" indicates the weft direction.

All the yarns used in manufacturing the present Knit B, namely the yarns threaded in guide-bars B2, B3 and B4, are made of a triblock copolymer with a central bloc of poly trimethylene carbonate (PTMC) and two lateral blocks of poly-L-lactide (PLLA) having a composition of about 80% lactide and 20% trimethylene carbonate. Knit B is fully bioresorbable.

The yarns threaded in guide-bars B2 and B3 are monofilaments having a diameter of 125 m. The yarn count is 156 dtex. Each threaded guide is threaded with two yarns.

The yarns threaded in guide-bar B4 are monofilaments having a diameter of 150 m. The yarn count is 227 dtex. Guide-bar B4 is single threaded.

The pattern repetition size of guide-bars B2 and B3 is 2 courses and the pattern repetition size of guide-bar B4 is 4 courses, so that the overall pattern repetition size is 4 courses (lines named 1' to 4' in FIG. 4).

The yarns threaded in B2 and B3 constitute the base of the present knit, since the hot-melt monofilament yarn, intended to generate the barbs, will be regularly cut during the melting step. The knitting patterns of guide-bars B2 and B3 produce an arrangement of yarns defining the two sides of the knit.

The knitting pattern repetition unit for guide-bars B2 and B3 includes a displacement of the yarns on 4 needles along 2 courses.

Such a knitting pattern repetition unit allows producing a knit having particularly good elasticity in all directions, while showing good mechanical properties, in particular excellent tensile breaking strength and bursting strength, good tear strength and suture pull-out strength.

Once the knit is produced, it is heat-set according to a conventional method, for example at 115° C., in order to stabilize it in length and width.

After the heat-setting step, the side of the knit from which the loops produced by guide-bar B4 protrude is placed in contact with a cylinder containing a heating resistor so as to melt the loops, for example in the same manner as described in WO01/81667. Like in Example 1, the heating resistor may show a temperature of about 250-290° C.

On melting, each loop cuts in two and gives rise to two barbs protruding outwards from said side of the knit.

The properties of the present knit B have been measured in the same manner and with the same methods as described in Example 1.

The results are collected in the Table II below:

TABLE II

| Property | Knit B |
| --- | --- |
| Surface density (g/m$^2$) | 144 |
| Pore size (mm$^2$) (width × height) | 1.7 × 1.4 |
| Gripping strength (N) | 72 ± 8 |

Example 3

In the present example, the mechanical properties of the knits of the invention of examples 1 and 2 above, namely Knit A and Knit B, have been measured according to the following methods:

Tensile breaking strength (N), tensile elongation at break (%), tensile elongation under 50N (%): are measured according to ISO 13934-1: 2013 *"Determination of breaking strength and elongation"*, 5 samples, width: 50 mm, length: 200 mm between the jaws, Crosshead speed: 100 mm/min, Pre-load: 0.5 N, using a traction testing machine such as the Hounsfield model H5KS (Hounsfield, Redhill, England), Bursting strength (kPa): measured according to ISO 13938-2: 1999 "Textiles—Bursting properties of fabrics—Pneumatic method for determination of bursting strength and bursting deformation", 5 samples using a Bursting strength tester, James Heal model Truburst 4, Suture pull out strength in the warp direction and in the weft direction measured as follows: a USP 2 suture yarn is passed through a pore of a 50×100 mm sample, at 10 mm from the edge of a small side of the sample, and is tracted away using a traction testing machine such as the Hounsfield model H5KS (Hounsfield, Redhill, England) with the following conditions: 5 samples, width 50 mm, 100 mm between the jaws, crosshead speed: 100 mm/min, Tear strength (N) in the warp direction and in the weft direction: measured according to superseded ISO 4674: 1977 *"Determination of tear resistance of coated fabrics"* Method A2, 5 samples, width: 75 mm, Tear length ≤145 mm, crosshead speed: 100 mm/min, In addition, these properties have been measured, according to the methods described above, for the following knits of the prior art:

Knit C: non bioresorbable knit for hernia repair made of polyester multifilaments, commercialized under the tradename «Parietex™ Hydrophilic 3 Dimensional Mes» by the company Sofradim Production, Knit D: non bioresorbable knit for hernia repair, made of a base knit of non bioresorbable polyester monofilaments and bioresorbable polylactic acid barbs, commercialized under the tradename «ProGrip™ Self-Gripping Polyester Mesh» by the company Sofradim Production.

The knits of the present examples are tested after their manufacture, without having been submitted to any fatigue and/or degradation treatment before the tests are completed.

The results are collected in Table III below:

TABLE III

| | Property | | | | | | | |
| --- | --- | --- | --- | --- | --- | --- | --- | --- |
| | Knit A | | Knit B | | Knit C | | Knit D | |
| Bursting strength (kPa) | 583 ± 20 | | 672 ± 60 | | 288 ± 15 | | 271 ± 5 | |
| | Warp | Weft | Warp | Weft | Warp | Weft | Warp | Weft |
| Tensile breaking strength (N) | 377 ± 15 | 323 ± 23 | 243 ± 37 | 345 ± 6 | 257 ± 17 | 117 ± 11 | 129 ± 9 | 179 ± 10 |
| Tensile elongation under 50 N (%) | 30 ± 1 | 38 ± 1 | 28 ± 1 | 31 ± 2 | — | — | 18 ± 1 | 23 ± 1 |
| Tensile breaking elongation (%) | 94 ± 2 | 97 ± 5 | 58 ± 5 | 77 ± 5 | 44 ± 5 | 63 ± 3 | — | — |
| Tear strength (N) | 66 ± 2 | 65 ± 6 | 36 ± 1 | 32 ± 3 | 17 ± 1 | 17 ± 3 | 18 ± 1 | 16 ± 3 |
| Suture pull-out strength (N) | 86 ± 6 | 69 ± 8 | 61 ± 6 | 44 ± 6 | 23 ± 4 | 27 ± 3 | 35 ± 4 | 25 ± 4 |

As can be observed from the results above, the knits A and B of the invention show excellent mechanical properties, such as a bursting strength of 583 kPa for Knit A and 672 kPa for Knit B, a tensile breaking strength in the warp direction of 377 N for Knit A and 243 N for Knit B, and a tensile breaking strength in the weft direction of 323 N for Knit A and 345 N for Knit B. In the same time, Knits A and B of the invention further show good elasticity with a tensile breaking elongation of 94% in the warp direction and a tensile breaking elongation of 97% in the weft direction for Knit A, and a tensile breaking elongation of 58% in the warp direction and a tensile breaking elongation of 77% in the weft direction for Knit B.

As a comparison, the non bioresorbable Knit C of the prior art shows a bursting strength of only 288 kPa, in other words representing only about 49% of the bursting strength of Knit A and only about 43% of the bursting strength of Knit B. The non bioresorbable Knit D of the prior art shows a bursting strength of only 271 kPa, in other words representing only about 46% of the bursting strength of Knit A and only about 40% of the bursting strength of Knit B.

As further appears from Table III above, the bioresorbable knits A and B of the invention show better mechanical properties, such as tensile breaking strength, tear strength and suture pull out strength, than the non bioresorbable Knits C and D of the prior art. The knits A and B of the invention further show better elasticity in all directions, as shown by the values measured for the tensile elongation under 50 N and the tensile breaking elongation, than the Knits C and D of the prior art.

Example 4

In the present example, the ball burst properties of knits A and B of the invention of examples 1 and 2 above are compared to that of knits of the prior art.

The ball burst test method used herein is in conformity with ASTM D6797-15 "Standard Test Method for Bursting strength of Textiles—Constant-rate-of-Extension (CRE) Ball Burst Test". This ball burst test is herein described with reference to FIG. 5. With reference to this figure, a square-shaped knit sample 1 of dimensions 6.5 cm×6.5 cm of the knit to be tested is secured between the lower jaw 2 and the upper jaw 3 of a ball burst strength tester 4, by a ring clamp having a 44.45 mm inner diameter. A 25.4 mm ball probe 5 is attached to the cross head 6 of a compression testing machine such as the Hounsfield model H5KS (Hounsfield, Redhill, England) and a preload of 0.1 N is applied to the sample 1.

Figure 5:
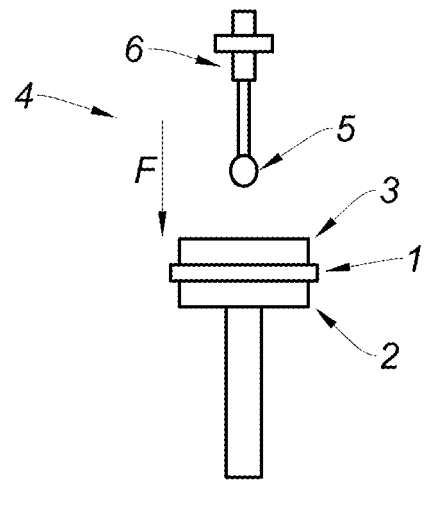
FIG. 5 is a schematic representation of the testing machine used in the ball burst test.

To complete the test, the ball probe 5 is moved downwards in the direction of the arrow F indicated on FIG. 5, thereby applying a force onto the sample 1. The ball probe is moved at a rate of 305 mm/min until the sample 1 fails.

The force (N) measured at the time of failure is referred to as the "Force max", and the displacement (mm) of the sample 1 at time of failure is referred to as "Deflection". The greater the Force max, the stronger the knit sample. The greater the deflection, the more elastic the knit. A knit having a high Force max and a high deflection is therefore a resistant knit that is capable of adapting smoothly to the pressure. A prosthesis for hernia repair made from such a knit will be resistant and conformable so that it is capable of bearing the pressures the abdominal wall is submitted to on a daily basis.

In addition to the two comparative Knits C and D described in Example 3, the following knits of the prior art are also tested in the present example:

Knit E: non bioresorbable knit for hernia repair made of polypropylene monofilaments, commercialized under the tradename "Optilene® Mesh LP" by the company B-Braun, Knit F: bioresorbable knit for hernia repair made of multifilaments of a copolymer of glycolide, lactide and trimethylene carbonate and of multifilaments of lactide and trimethylene carbonate, commercialized under the tradename "Tigr® Matrix" by the company Novus Scientific.

1) Ball Burst Test at Time T0:

The knits A-F have been tested at time T0, without having been submitted to any fatigue and/or degradation treatment before completion of the test.

The results of the test completed at T0 are collected in Table IV below:

TABLE IV

| Force max and deflection at T0 | | |
| --- | --- | --- |
| Tested Knit | Force max (N) | Deflection (mm) |
| Knit A | 506 ± 16 | 25 ± 1 |
| Knit B | 367 ± 54 | 17 ± 1 |
| Knit C | 187 ± 13 | 16 ± 1 |
| Knit D | 195 ± 16 | 21 ± 2 |
| Knit E | 273 ± 20 | 22 ± 1 |
| Knit F | 463 ± 4 | 19 ± 0 |

As appears from Table IV, knits A and B of the invention show a high Force max and a high deflection at time T0. These knits are therefore particularly suitable for use as hernia repair as they are strong and adaptable.

2) Ball Burst Test after 20 Weeks of Static Degradation In Vitro:

The bioresorbable knits A, B and F have further been tested after having been immersed in a static manner during 20 weeks (T20ws) in a buffer solution intended to simulate physiological fluid in a human body, in order to evaluate the behavior of the knit under such conditions. The testing is performed in accordance to the norm ISO 13781: 1997, with the following deviations: oven precision is +2° C., and the buffer is changed when the pH drops below 7.2.

The knit samples are immersed in a phosphate buffer solution consisting of potassium dihydrogen phosphate and disodium hydrogen phosphate in sterile water at a concentration of $\frac{1}{15}$ mol/L. The pH value of the buffer solution is 7.4±0.1.

Samples of dimensions 7×7 cm are placed in a sterile 180 mL polypropylene container filled with 150 mL phosphate buffer solution. The containers are closed and placed into a climate chamber at 37° C. in which they are maintained in a static state during 20 weeks.

After 20 weeks, each sample is removed from the solution and is directly tested for ball burst as described above.

The results of the test completed at T20ws are collected in Table V below:

TABLE V

| Force max and deflection at T20 ws | | |
| --- | --- | --- |
| Tested Knit | Force max (N) | Deflection (mm) |
| Knit A | 539 ± 29 | 25 ± 1 |
| Knit B | 368 ± 21 | 16 ± 1 |
| Knit F | 143 ± 3 | 19 ± 1 |

As appears from Table V above, the knits A and B of the invention have maintained their ball burst properties, even after having been immersed 20 weeks in the buffer solution in which they have been partially degraded. Indeed, for these two knits, the values of the Force max and of the deflection remain substantively the same at T0 and at T20ws.

As a comparison, the Force max of comparative bioresorbable Knit F has gone from 463 N to 143 N after static immersion during 20 weeks in the buffer solution, thereby losing about 69% of its initial value. As a result, the Force max of comparative Knit F at T20ws represents around 26% only of the Force max measured for inventive Knit A and around 39% only of the Force max measured for inventive Knit B.

For comparison's sake, the values of the ball burst properties of non bioresorbable comparative knits C, D and E at T0 on one hand, and of inventive knits A and B at T20ws on the other hand, are recalled in one single Table VI below, in order to emphasize that the knits of the invention show better ball burst properties after 20 weeks of static degradation treatment than non bioresorbable knits of the prior art which have not been submitted to any degradation treatment:

TABLE VI

| comparison of ball burst properties at T0 for non bioresorbable knits of prior art and at T20 ws for bioresorbable knits of the invention | | |
|---|---|---|
| Tested Knit | Force max (N) | Deflection (mm) |
| Knit A (at T20 ws) | 539 ± 29 | 25 ± 1 |
| Knit B (at T20 ws) | 368 ± 21 | 16 ± 1 |
| Knit C (at T0) | 187 ± 13 | 16 ± 1 |
| Knit D (at T0) | 195 ± 16 | 21 ± 2 |
| Knit E (at T0) | 273 ± 20 | 22 ± 1 |

Example 5

In the present example, the mechanical properties of knits A and B of the invention of examples 1 and 2 above are compared to that of comparative bioresorbable knit F of the prior art. The knits are first tested at time T0, i.e. without having been submitted to any fatigue and/or degradation treatment.

The knits A and B of the invention are also tested at time T20ws, i.e. after 20 weeks of in vitro static degradation, the static degradation protocol being identical to that described in Example 4 above.

The comparative Knit F is further tested at time T13ws, i.e. after 13 weeks of in vitro static degradation, the static degradation protocol being identical to that described in Example 4 above, except that the samples are removed from the buffer solution after 13 weeks of immersion instead of 20 weeks.

The mechanical properties of the knits are measured according to a uniaxial tensile test that has been adapted to small sizes samples as follows: tensile breaking strength (N), tensile elongation at break (%), tensile elongation under 50N (%) and tensile elongation under 30 N (%) are measured according to ISO 13934-1: 2013 "Determination of breaking strength and elongation", with the following deviations: 5 samples each direction: dimensions 25 mm×60 mm—Length: 40 mm between the jaws, Crosshead speed: 20 mm/min, Pre-load: 0.5 N, using a traction testing machine such as a Hounsfield model H5KS.

The results are collected in the following Table VII and Table VIII:

TABLE VII

| breaking strength and elongation properties at T0 | | | | | |
|---|---|---|---|---|---|
| | Property | | | | |
| | Knit A | | Knit B | | Knit F | |
| | Warp | Weft | Warp | Weft | Warp | Weft |
| Breaking strength (N) | 165 ± 11 | 145 ± 5 | 106 ± 8 | 156 ± 11 | 175 ± 11 | 180 ± 9 |
| Elongation under 30 N (%) | 33 ± 2 | 38 ± 1 | 33 ± 2 | 31 ± 3 | 19 ± 1 | 13 ± 0 |
| Elongation under 50 N (%) | 46 ± 2 | 50 ± 2 | 43 ± 2 | 40 ± 3 | 27 ± 1 | 20 ± 0 |
| Breaking elongation (%) | 95 ± 6 | 98 ± 5 | 68 ± 4 | 80 ± 2 | 79 ± 7 | 61 ± 2 |

TABLE VIII

| breaking strength and elongation properties at T20 ws | | | | |
|---|---|---|---|---|
| | Knit A | | Knit B | |
| Property | Warp | Weft | Warp | Weft |
| Breaking strength (N) | 164 ± 10 | 138 ± 5 | 107 ± 10 | 148 ± 25 |
| Elongation under 30N (%) | 32 ± 1 | 38 ± 2 | 30 ± 3 | 28 ± 5 |
| Elongation under 50N (%) | 45 ± 1 | 49 ± 2 | 42 ± 4 | 39 ± 5 |
| Breaking elongation (%) | 97 ± 4 | 98 ± 5 | 69 ± 2 | 81 ± 8 |

As is clear from Table VII and Table VIII above, the knits A and B of the invention have maintained their breaking strength and elongation properties at a high level, even after having been submitted to a static degradation treatment during 20 weeks. Indeed, for these two knits, the values of the breaking strength, elongation under 30 N, elongation under 50 N and breaking elongation remain substantively the same at T0 and at T20ws. This means that a prosthesis for hernia repair made from inventive knits A or B will be able to remain as mechanically resistant and elastic after 20 weeks as at the time it is manufactured. Such a prosthesis will therefore be capable of resisting to and conform to the various pressures the abdominal wall of a human body is submitted to during his daily life.

For comparative Knit F, the breaking strength according to the uniaxial tensile test described above for small size samples has been measured after 13 weeks (T13ws) of static degradation, where the static degradation protocol is identical as that described above, except that tests are performed after 13 weeks immersion in the buffer solution instead of 20 weeks.

The results are collected in Table IX below:

TABLE IX

| breaking strength for Knit F at T13 ws | | |
|---|---|---|
| | Knit F | |
| Property | Warp | Weft |
| Breaking strength (N) | 73 ± 9 | 33 ± 4 |

As shown by these results, after 13 weeks of static degradation, the breaking strength of the comparative bioresorbable knit F has gone from 175 N to 73 N in the warp direction, meaning that it has lost 58% of its initial value, and from 180 N to 33 N in the weft direction, meaning that it has lost 81% of its initial value. The values measured at T13ws for comparative Knit F are inferior to that measured at T20ws for Knits A and B of the invention, despite a much lower time spent under the degradation conditions.

Example 6

In the present example, the breaking strength of inventive knits A and B of examples 1 and 2 above has been measured according to the conditions of the uniaxial tensile test adapted to small size samples as described at Example 5 above, after having submitted the knits to a period of in vitro dynamic degradation of 20 weeks (T20wd) as described below.

In Vitro Dynamic Degradation Protocol:

A device equipped with several 100 N load cells, each cell having a first fixed jaw capable of grasping a first knit sample edge and a second moving jaw capable of grasping the opposite edge of the knit sample is provided. The device and the cells are immersed in a temperature controlled bath at 37° C. The bath is a phosphate buffer solution consisting of potassium dihydrogen phosphate and disodium hydrogen phosphate in sterile water at a concentration of $\frac{1}{15}$ mol/L. The pH value of the buffer solution is 7.4±0.1.

Knit samples of dimensions 60 mm×25 mm are prepared. Each sample is attached to the jaws of one cell. The length between the jaws is 40 mm. The moving jaw is moved away and closer to the fixed jaw in accordance to a uniaxial cyclic sine wave oscillating between 6 and 8 mm displacement so as to cause a 15% to 20% deformation of the knit sample at a frequency of 1 Hz. Such a fatigue treatment is supposed to approximate the anticipated mechanical loading of a knit implanted in the abdominal wall of a human body.

The samples are submitted to such a fatigue treatment during 20 weeks in a continuous manner.

The protocol described above is intended to simulate the dynamic degradation conditions to which a prosthetic knit may be submitted to once it is implanted in the body of a patient, in order to evaluate the expected behavior of the knits under such conditions.

Measure of the Breaking Strength:

After 20 weeks of dynamic degradation treatment above, referred to as time T20wd, each sample, maintained in wet conditions by being immersed for 1 h in sterile water at 37° C., is tested for tensile breaking strength as described in Example 5.

The results are collected in Table X below.

TABLE X

| | breaking strength at T20 wd | | | |
| | Knit A | | Knit B | |
| Property | Warp | Weft | Warp | Weft |
| Breaking strength (N) | 123 ± 12 | 115 ± 2 | 75 ± 5 | 104 ± 5 |

For comparison's sake, the breaking strength of comparative non bioresorbable knits C, D and E has also been measured according to the conditions of the uniaxial tensile test adapted to small size samples as described in Example 5 above, at T0, the knits being submitted to no fatigue and/or degradation treatment before completion of the test.

The values of the breaking strength of non bioresorbable knits C, D and E at T0 on one hand, and of inventive knits A and B both at T20ws and at T20wd on the other hand, are collected in one single Table XI below, in order to emphasize that the knits of the invention show better breaking strength properties after 20 weeks of static degradation treatment (T20ws) or after 20 weeks of dynamic degradation treatment (T20wd) than non bioresorbable knits of the prior art which have not been submitted to any degradation treatment.

TABLE XI comparison of breaking strength at T0 for non bioresorbable knits of prior art and at T20 ws and T20 wd for bioresorbable knits of the invention

| | Breaking strength (N) | |
| Tested Knit | Warp | Weft |
| Knit A (at T20 ws) | 164 ± 10 | 138 ± 5 |
| Knit A (at T20 wd) | 123 ± 12 | 115 ± 2 |
| Knit B (at T20 ws) | 107 ± 10 | 148 ± 25 |
| Knit B (at T20 wd) | 75 ± 5 | 104 ± 5 |
| Knit C (at T0) | 81 ± 8 | 51 ± 4 |
| Knit D (at T0) | 49 ± 10 | 79 ± 8 |
| Knit E (at T0) | 71 ± 10 | 33 ± 8 |

Example 7

In the present example, knits A and B of examples 1 and 2 above have been implanted in vivo in swines in order to evaluate the capabilities of the knits of the invention to reinforce, over time, a repaired ventral abdominal wall defect in a porcine model. The performance of knits A and B regarding ball burst properties after a certain time of implantation have been compared to that of a native abdominal wall on one hand, and to that of a wall for which the defect has been simply sutured without any reinforcement knit at all.

The protocol followed for the present study is the following one. The four following treatments, including optionally surgical repair, have been applied:

Treatment 1: Negative Control: a disc-shaped defect of 3 cm diameter is created in the ventral abdominal wall of the animal. Surgical repair consists in simply closing the defect with absorbable suture with no use of reinforcement knit.

Treatment 2: Positive Control: corresponds to the native abdominal wall. No defect is created. No surgical repair is performed.

Treatment 3: Knit A: a disc-shaped defect of 3 cm diameter is created in the ventral abdominal wall of the animal in the same manner as in Treatment 1. Surgical repair consists in closing the defect with absorbable suture and reinforcing the abdominal wall with a disc-shaped sample of Knit A of Example 1 above, having a diameter of 9 cm.

Treatment 4: Knit B: a disc-shaped defect of 3 cm is created in the ventral abdominal wall of the animal in the same manner as in Treatment 1 and Treatment 2 above. Surgical repair consists in closing the defect with absorbable suture and reinforcing the abdominal wall with a disc-shaped sample of Knit B of Example 2 above, having a diameter of 9 cm.

20 weeks after surgical repair, the animals are euthanized. Abdominal wall samples are collected as follows: each site (native wall for Treatment 2 or repaired defect sites for Treatments 1, 3 and 4), and an appropriate amount of surrounding tissue, are explanted, trimmed, wrapped in saline soaked gauze and subjected to ball burst testing according to the method described in Example 4 above in which the knit sample is replaced by the abdominal wall sample.

Figure 6:
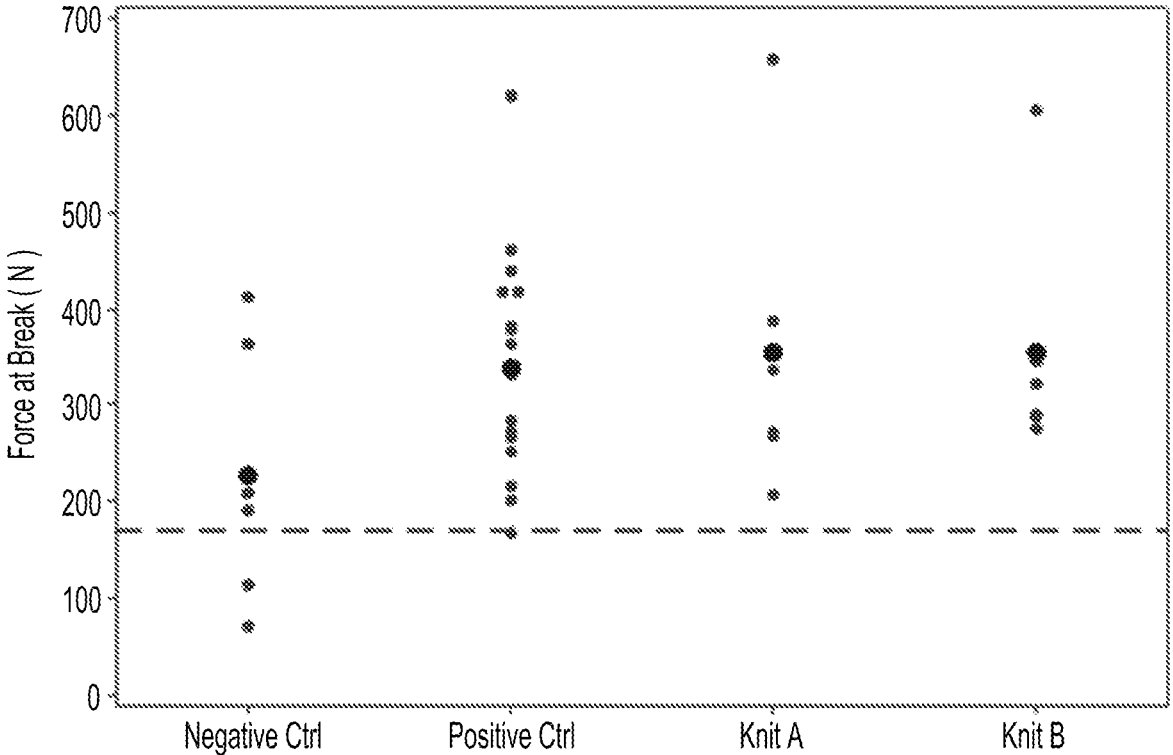
FIG. 6 is a graph showing the distribution of the Force max measured for different wall abdominal samples in relation to the in vivo study described at Example 7.

FIG. 6 reproduces a graph showing the distribution of the Force max measured for the different Treatments above, namely the Negative Control, the Positive Control, Knit A and Knit B.

The dotted line of the graph of FIG. 6 represents 80% of the value of the Force max for the native abdominal wall.

As appears from this Figure, the knits of the invention show, 20 weeks after implantation, in other words about 5 months after implantation, a Force max that is well above 80% of the Force max of the native abdominal wall.

As a result, the implanted knits of the invention still contribute to the repair of the abdominal wall at the end of the critical period of healing of at least 5 months as defined above.

What is claimed is:

1. A bioresorbable prosthetic porous knit including barbs protruding outwards from at least one side thereof, the knit comprising an arrangement of yarns of bioresorbable biocompatible material, the arrangement of yarns including at least a first yarn and a second yarn defining at least two sides for said porous knit, the porous knit produced on a knitting machine including at least two guide bars B2, B3, following a standard ISO 11676 knit pattern below:

B2: 1-0/3-4//

B3: 3-4/1-0//, wherein guide bar B2 is double threaded with the first yarn and guide bar B3 is double threaded with the second yarn.

2. The bioresorbable prosthetic knit according to claim 1, wherein the first and second yarns of the arrangement defining the two sides of the porous knit are monofilaments showing a diameter ranging from about 80 to about 140 μm.

3. The bioresorbable prosthetic knit according to claim 2, wherein the monofilaments have a diameter of about 125 μm.

4. The bioresorbable prosthetic knit according to claim 1, wherein the bioresorbable biocompatible material of the first and second yarns is a copolymer of poly trimethylene carbonate (PTMC) and of poly-L-lactide (PPLA).

5. The bioresorbable prosthetic knit according to claim 4, wherein the bioresorbable biocompatible material includes 80% lactide and 20% trimethylene carbonate.

6. The bioresorbable prosthetic knit according to claim 1, wherein the porous knit displays a tensile elongation under 50 N from about 20% to about 35% in the warp direction and from about 20% to about 45% in the weft direction.

7. The bioresorbable prosthetic knit according to claim 1, wherein the porous knit displays a Force max at T0 from about 300 N to about 600N and a Force max at T20ws from about 300 N to about 600N.

8. The bioresorbable prosthetic knit according to claim 1, wherein the porous knit displays a Force max that remains substantively the same at T0 and at T20ws.

9. The bioresorbable prosthetic knit according to claim 7, wherein the porous knit further displays a deflection at T0 ranging from about 15 mm to about 30 mm and a deflection at T20ws ranging from about 15 mm to about 30 mm.

10. The bioresorbable prosthetic porous knit according to claim 1, wherein the porous knit displays a tensile breaking elongation from about 40% to about 100% in the warp direction and from about 60% to about 110% in the weft direction.

11. The bioresorbable prosthetic porous knit according to claim 1, wherein the porous knit displays an elasticity in all directions.

12. The bioresorbable prosthetic knit according to claim 1, wherein the arrangement of yarns further includes a third yarn configured to form the barbs, guide bar B4 single threaded with the third yarn following a standard ISO 11676 knit pattern below:

B4: 5-5/2-3/0-0/3-2//.

13. A bioresorbable prosthetic porous knit comprising an arrangement of yarns including at least a first yarn and a second yarn of bioresorbable biocompatible material defining at least two sides for said porous knit, the porous knit produced on a knitting machine including at least two guide bars B2, B3, following a standard ISO 11676 knit pattern below:

B2: 1-0/3-4//

B3: 3-4/1-0//, wherein guide bar B2 is double threaded with the first yarn and guide bar B3 is double threaded with the second yarn.

14. The bioresorbable prosthetic knit of claim 13, wherein the porous knit is a self-gripping porous knit.

15. The bioresorbable prosthetic knit of claim 13, wherein the porous knit displays a gripping strength ranging from about 60 N to about 160 N.

16. The bioresorbable prosthetic knit of claim 13, the knitting machine further comprising guide bar B4 single threaded with a third yarn.

17. The bioresorbable prosthetic knit according to claim 16, wherein guide bar B4 follows a standard ISO 11676 knit pattern below:

B4: 5-5/2-3/0-0/3-2//.

18. The bioresorbable prosthetic knit according to claim 13, wherein the porous knit further displays:

a Force max at T0 from about 300 N to about 600N and a Force max at T20ws from about 300 N to about 600N; and a deflection at T0 ranging from about 15 mm to about 30 mm and a deflection at T20ws ranging from about 15 mm to about 30 mm.

* * * * *